United States Patent

Taniji et al.

[11] Patent Number: 5,598,841
[45] Date of Patent: Feb. 4, 1997

[54] BLOOD FLOW MEASUREMENT SYSTEM

[75] Inventors: Ayafumi Taniji; Koji Katayama; Satohiko Takanashi, all of Tsukuba, Japan

[73] Assignee: Kowa Company Ltd., Japan

[21] Appl. No.: 306,379

[22] Filed: Sep. 15, 1994

[30] Foreign Application Priority Data

Sep. 24, 1993 [JP] Japan .................................. 5-237089

[51] Int. Cl.$^6$ .................................................. A61B 5/026
[52] U.S. Cl. .......................... 128/634; 128/664; 128/666; 128/691
[58] Field of Search .................................. 128/633–634, 128/664–666, 691; 356/39–41

[56] References Cited

U.S. PATENT DOCUMENTS

| | | | |
|---|---|---|---|
| 4,596,254 | 6/1986 | Adrian et al. | 128/666 |
| 4,862,894 | 9/1989 | Fujii | 128/666 |
| 5,361,769 | 11/1994 | Nilsson | 128/666 |

FOREIGN PATENT DOCUMENTS

| | | | |
|---|---|---|---|
| 0488614 | 6/1992 | European Pat. Off. | 128/666 |
| 2531854 | 2/1984 | France | 128/666 |

*Primary Examiner*—Ruth S. Smith
*Attorney, Agent, or Firm*—Adams & Wilks

[57] ABSTRACT

A blood flow measurement system for measuring blood flow rate and blood flow velocity comprises a circuit device for irradiating an in vivo tissue measurement subject with coherent light, a light receiving element for receiving scattered light from the in vivo tissue, a converter for converting an intensity of the received scattered light into an electric signal, a circuit device for calculating a power spectrum of the time-course variation of the scattered light intensity, a device for plotting the power spectrum in a semilogarithmic coordinate system having a logarithmic vertical axis, and a device for linearly approximating a prescribed frequency component of the semilogarithmic power spectrum and calculating a slope and a y intercept of the power spectrum curve. The blood flow velocity can be determined from the slope of the curve approximating the power spectrum, while blood flow rate can be determined from the slope and y intercept of the curve approximating the power spectrum.

21 Claims, 11 Drawing Sheets

BLOOD FLOW MEASUREMENT SYSTEM

BACKGROUND OF THE INVENTION

1. Field of the Invention

This invention relates generally to a blood flow measurement system, and more particularly to a blood flow measurement system for obtaining blood flow rate, blood flow velocity and other blood flow information based on the intensity of scattered light received from in vivo tissue irradiated with coherent light.

2. Description of the Prior Art

Apparatuses used for obtaining blood flow data include electromagnetic stromuhrs for use with a single blood vessel and laser stromuhrs for noninvasive optical measurement of blood flow at the skin surface.

In the electromagnetic stromuhr, a measurement probe including a magnetic pole for producing a magnetic field and an electrode for detecting electromotive force is attached to the blood vessel so as to enclose it and the mean flow velocity of erythrocytes flowing through the probe is measured. Based on the assumption that the inside diameter of the measurement probe attached to the blood vessel is equal to the diameter of the blood vessel, the sectional area of the blood vessel is defined in terms of the sectional area of the measurement probe.

The blood flow rate is therefore calculated from the product of the average flow velocity and the sectional area of the probe. A problem tends to arise when the measurement is conducted at multiple points on a plurality of closely spaced blood vessels, however, because electromagnetic induction occurring between proximate measurement probes may interfere with the measurement.

On the other hand, the laser stromuhr enables noninvasive measurement of changes in blood flow in the skin and outputs a value corresponding to the blood flow. The laser stromuhr receives as its signal the light scattered from large numbers of erythrocytes flowing through the in vivo tissue. By frequency analyzing the light quantity as it varies with time owing to the mutual interference among the scattered light rays from the large number of erythrocytes, it extracts a quantity dependent on the macroscopic flow velocity of the large number of erythrocytes and a quantity corresponding to the number of erythrocytes in the irradiated region and calculates the blood flow value.

The prior art technologies are characterized by the methods they use for frequency analysis of the light quantity variation. For example, in one of these methods the value F corresponding to the blood flow rate is defined as $$F = \int_0^\infty \omega P(\omega) d\omega$$

where $\omega$ is the angular frequency and $P(\omega)$ is the power spectral density. (See: Nilsson, G. E., Tenland, T. and Oberg, P. A.: Evaluation of a laser Doppler flow meter for measurement of tissue blood flow. IME-27, 597–604, 1980) In another method described in Japanese Patent Laid-open Publication No. Sho 60(1985)-203235, for example, the power spectrum obtained by frequency analysis is plotted in a full logarithmic coordinate system and the slope is defined as the value corresponding to the skin blood flow.

When the performances of the prior art apparatuses were compared by measuring the flow of light-scattering particles as a simulated blood flow, it was found that the coefficient between the flow velocity and the output value from the apparatus is different due to the difference in adopted methods. (See: Okada, H., Fukuoka, Y, Minamidani, H., Sekizuka, E., Ohtzuka, T. and Bokuzawa, S: Problems concerning quantitativeness of laser system stromuhr. Papers to be read at the Fourth Japanese ME Association Autumn Conference, Medical Electronics and Bioengineering, Vol. 27, Special Autumn Edition (1989))

Moreover, actual measurements have to be made in the presence of movement and vibration caused by the respiration, pulsation etc. of the living tissue that is the measurement subject. Different systems treat these external disturbances differently and the electrical low-pass filters they use for averaging over time have different characteristics. Time response characteristics are often sacrificed in order to achieve stable measurement.

Japanese Patent Laid-open Publication Nos. Hei 4(1992)-193158 and 4(1992)-193159 teach multiple point measurement methods. Specifically, japanese Patent Laid-open Publication No. Hei 4(1992)-193159 teaches an apparatus and method for deriving two dimensional blood flow information by scanning a laser beam intermittently so as to repeatedly move and stop the beam spatially and obtaining scattered light information relating to the blood flow in the in vivo tissue when the beam is stopped. In order to measure a large number of points within a two-dimensional plane as quickly as possible by this method, it is necessary to suppress the effect of vibration on the measurement at the measurement points while also conducting the measurement with good time response characteristics. The maintenance of the time response characteristics is of importance also in the measurement by points.

The comparison between the electromagnetic stromuhr and the laser stromuhr shows that, owing to its measurement principle, the laser stromuhr is free of the problem of magnetic inductance between measurement probes experienced by the electromagnetic stromuhr discussed earlier and, as such, has the advantage of being able to bring the measurement points close together for measuring the blood flow rate in a plurality of closely spaced blood vessels. If, therefore, a stromuhr operating on the principle of measuring scattered laser light could be used in place of the probes of an electromagnetic stromuhr, the problem of magnetic induction between measurement probes would no longer have to be taken into account.

Use of a laser stromuhr in place of an electromagnetic stromuhr for directly displaying blood flow rate is in fact difficult, however, because current laser stromuhrs produce measurement values that change with the individual measurement conditions and are able to display only a relative value or the amount of change.

The inventor's approach to improving the poor time response of the prior art laser stromuhr and overcoming its drawback of being able to display only relative values was to focus on improving the method of analyzing the time-course variation components of the scattered light quantity.

For improving the accuracy of signal analysis it is necessary to extract the substantial characteristics of the power spectrum without interference from noise. Research has been directed to signal processing methods that presume a peak frequency, a maximum frequency or the like within a specific frequency band, however, in large part because it has been held possible to obtain a Doppler signal with respect to the scattered light signal generation mechanism.

In fact, however, the practically obtainable electric signal does not include the peak frequency peculiar to a Doppler signal and is observed as a dynamic speckle signal caused by the mutual interference between scattered light beams from the moving light-scattering particles. It is therefore appropriate to provide a method of the signal processing based on the concerning signal characteristics and it is effective to provide an analysis method that takes the characteristics of the power spectrum function into account.

The conventional method of removing noise has been to measure the power spectrum of the dark noise and to remove the measured component from the power spectrum at the time of measuring the blood flow, thus calculating the power spectrum for a subject under measurement. Since the noise component is also generated at the time of measurement, however, it is preferable from the viewpoint of signal processing to estimate the noise component from the measured power spectrum and then remove it.

On the other hand, a method which attempts to remove the noise component by taking the average of the power spectrum over time has also been adopted. Since this involves the integration of a signal that varies with time, however, it sacrifices the time response characteristics and, while stable, requires sampling over long periods during which the measurement subject has to be restrained. In some cases, therefore, there is a restriction on the type of subject.

SUMMARY OF THE INVENTION

One object of the invention is therefore to provide a flow measurement system utilizing a laser beam that is arranged to establish an analysis method which is little affected by vibration etc. of the subject during measurement and which enables high-accuracy measurement in a short period of time.

Another object of the invention is to provide a blood flow measurement system constituting an improvement in the arrangement of the stromuhr that utilizes measurement of scattered laser light and is characterized in not giving rise to induction between probes as occurs in the electromagnetic stromuhr, the improvement enabling the stromuhr to ascertain the absolute blood flow velocity and blood flow rate during measurement with respect to a single blood vessel.

In this invention, based on the knowledge that a power spectrum function can be treated as an exponential function, a signal processing method was developed that is characterized by, inter alia, noise separation through exponential function fitting and extraction of frequency components from an attenuation coefficient, whereby it was found that blood flow information could be effectively derived.

The invention achieves the aforesaid objects by providing a blood flow measurement system comprising means for irradiating an in vivo tissue measurement subject with coherent light, means for receiving scattered light from the in vivo tissue, means for converting the intensity of the received scattered light into an electric signal, means for calculating the power spectrum of the time-course variation of the scattered light intensity, and means for plotting the power spectrum in a semilogarithmic coordinate system having a logarithmic vertical axis, information relating to blood flow being obtained based on the results obtained by conducting prescribed function fitting with respect to a prescribed frequency component of the semilogarithmical power spectrum.

In the thus arranged system, blood flow rate, blood flow velocity and other blood flow information can be secured by calculating the power spectrum of the time-course variation of the scattered light intensity and carrying out prescribed function fitting with respect to a prescribed frequency component of the power spectrum. Moreover, by limiting the measurement to that of the prescribed frequency components of the power spectrum, it is possible to avoid the effect of vibration and other noise components.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

Figure 1:
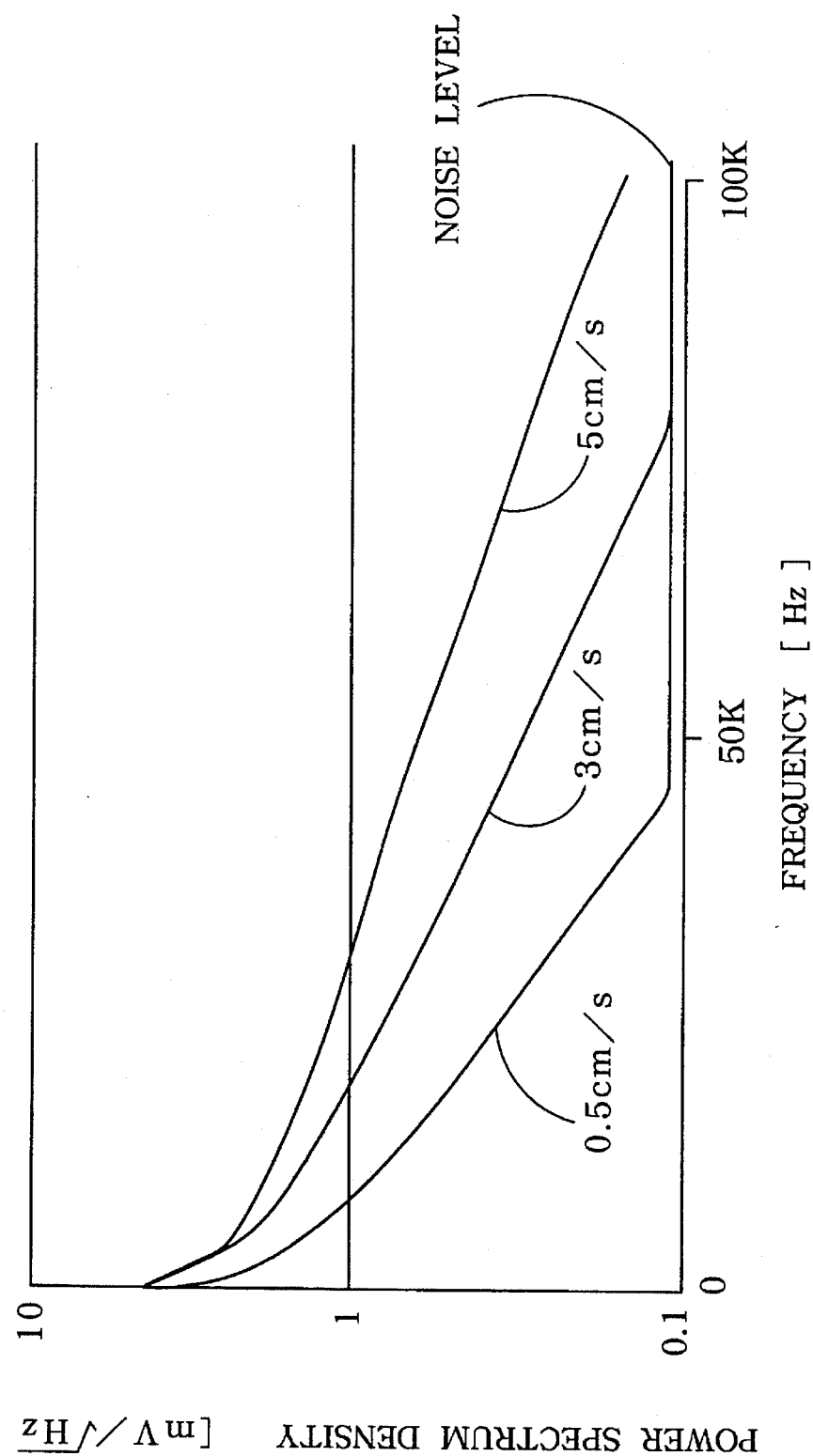
FIG. 1 is a graph showing the power spectrum of received scattered light when the exposed carotid of a live rabbit is irradiated with a laser beam.

The invention will now be described in detail on the basis of the preferred embodiments illustrated in the drawings.

FIG. 1 shows the power spectrum of received scattered light when the exposed carotid of a live rabbit is irradiated with a laser beam. The horizontal axis representing frequency in this graph is scaled arithmetically while the vertical axis is scaled logarithmically. The power spectrum is linear except in the low-frequency region. The value at the end of each lead line in this graph was obtained by simultaneously monitoring the blood flow rate with an electromagnetic stromuhr, and the slopes of the straight lines are the reciprocals of the blood flow velocities. The power spectrum density can therefore be approximated relative to frequency as $$\log = (P(f)) = H - \frac{c}{v} f \qquad (1)$$

where:

log: natural logarithm
P(f): power spectrum density distribution
H: log of DC light intensity
f: frequency
v: flow velocity
c: Conversion coefficient to electromagnetic stromuhr results Therefore, since it follows that $$P(f) = h\exp\left(-c\frac{f}{v}\right) \quad (2)$$

where:

P(f): power spectrum density distribution
h: DC light intensity
f: frequency
v: flow velocity
c: Conversion coefficient to electromagnetic stromuhr results, the power spectrum of the intensity of the scattered light from the erythrocytes flowing through a blood vessel can be approximated as an exponential function.

Therefore, by obtaining the semilogarithmic distribution of the power spectrum and using the method of least squares to fit Eq. 1 to the result, it is possible to obtain the flow velocity v and the y intercept H.

Another possible method is to fit Eq. 2. In this case, the 1/e width of the fitted exponential function corresponds to the flow velocity.

In addition, the area of the approximated exponential function can be used as a value representing the number of erythrocytes flowing through the irradiated region. Defining the quantity corresponding to the number of erythrocytes as S, we have $$S = \int_0^\infty h\exp\left(-c\frac{f}{v}\right) df = \frac{v}{c} h \quad (3)$$

and the blood flow rate which is the product of the flow velocity and the number of erythrocytes can be obtained as $$F = h\left(\frac{v}{c}\right)^2 \quad (4)$$

Although vibration caused by respiration and the like destabilizes the measurement in the low-frequency region, problems related to vibration can be overcome by presuming the function to be exponential and fitting it in the range of a power spectrum of several hundred Hz, preferably over around 500 Hz. When this method is used, the power of the scattered light intensity including the DC component h can be obtained without including the low-frequency region that is easily affected by vibration in the measurement region.

Figure 2:
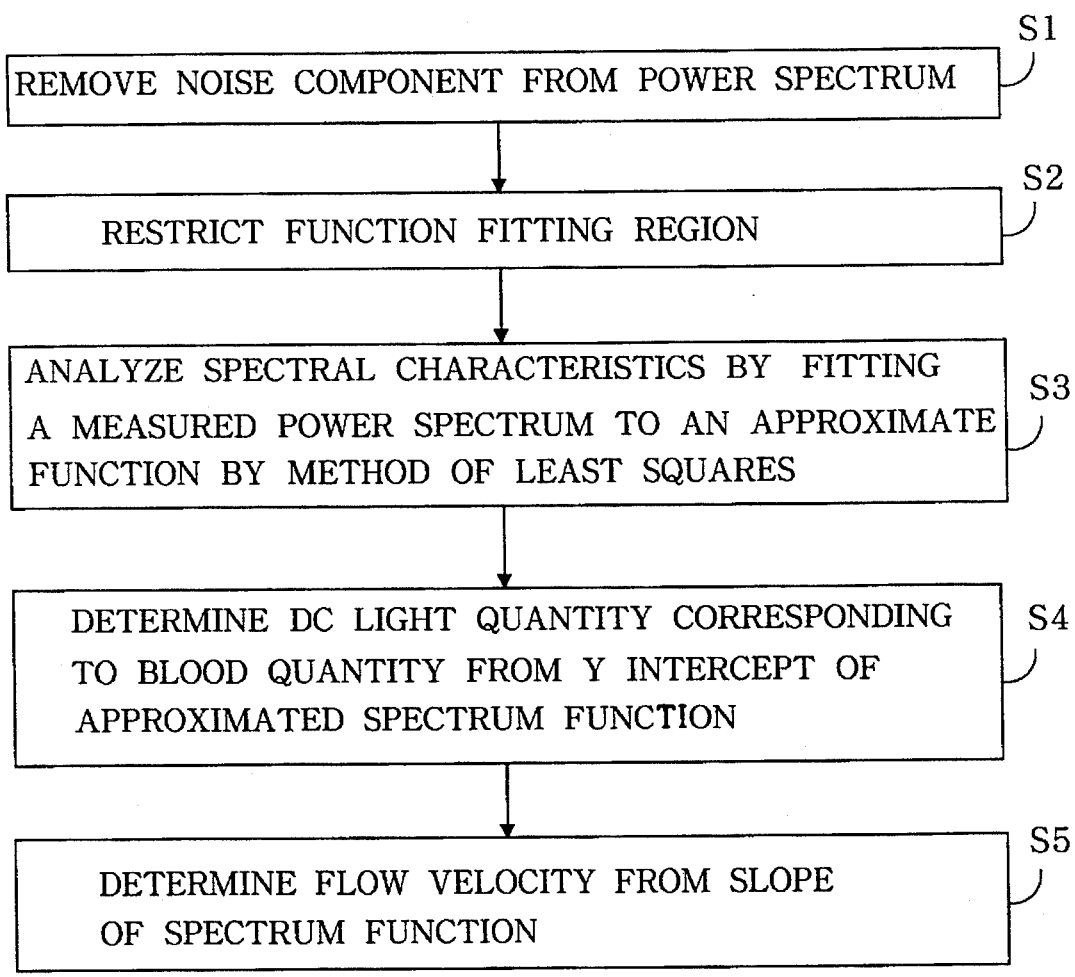
FIG. 2 is a flowchart summarizing the analysis procedures according to the invention.

The foregoing procedures are summarized in FIG. 2, which shows an analysis procedure for deriving scattered light component and velocity component corresponding to blood flow rate solely from AC signal of dynamic speckle signal. Noise removal by region designation and designation of the function fitting region are conducted in steps S1 and S2, while steps S3, S4 and S5 are for function fitting Eq. 1 by least square approximation, calculating the blood quantity and the DC light quantity, and determining the flow velocity.

Figure 3:
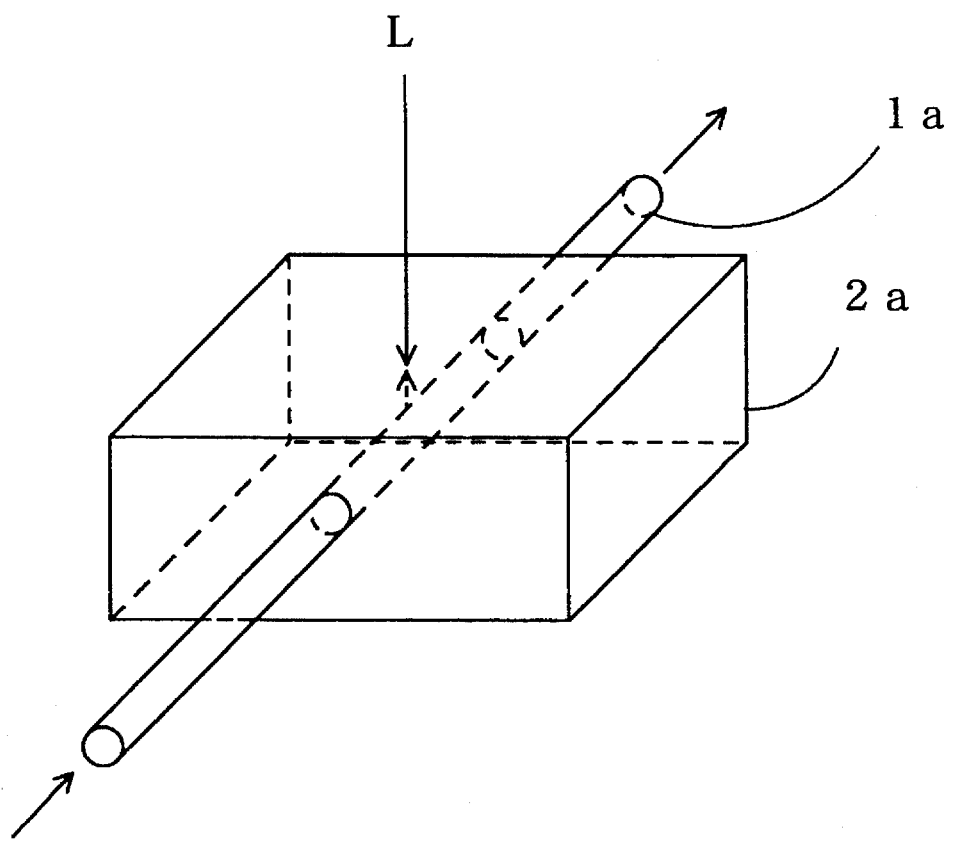
FIG. 3 is an illustrative view for explaining the structure of a blood flow measurement model.

The validity of the foregoing analysis method was checked using a model in which, as shown in FIG. 3, blood or a suspension of polystyrene latex particles was passed through a silicon tube 1a enclosed within a Teflon block 2a.

Figure 4:
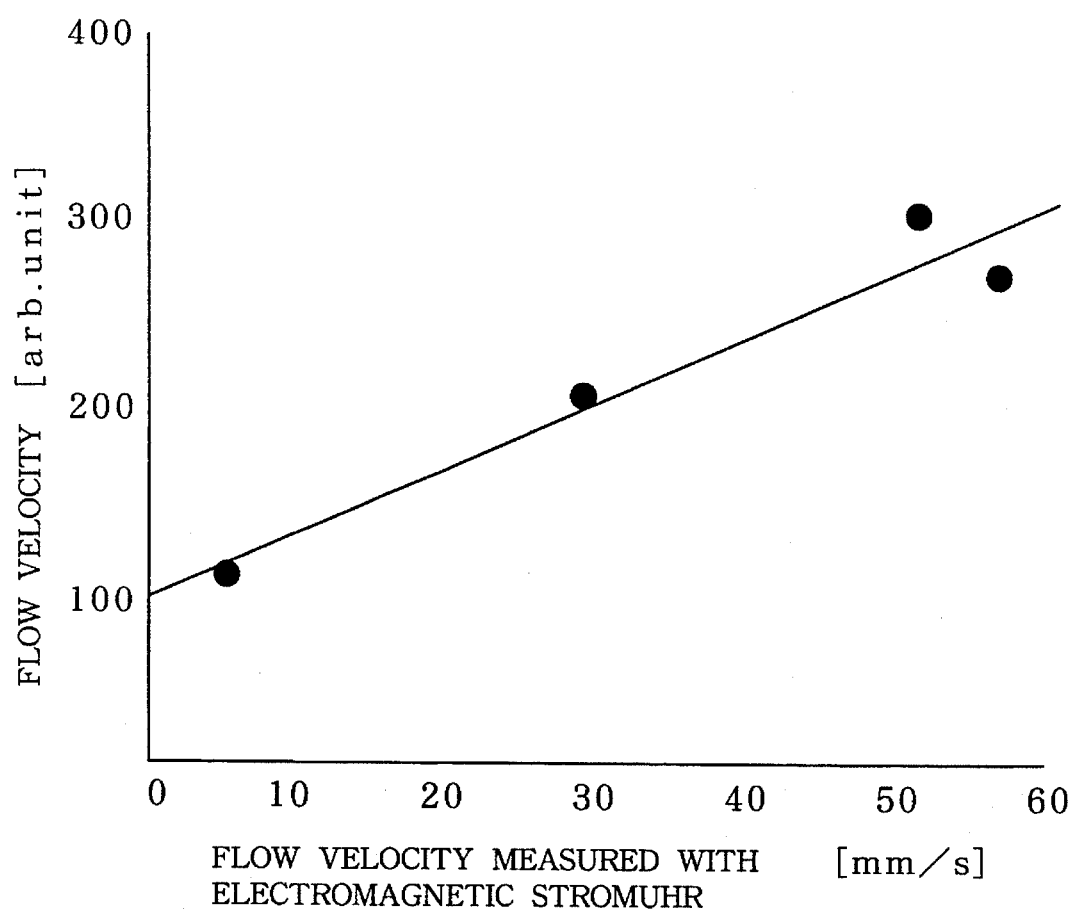
FIG. 4 is a graph showing the result of blood flow measurement on the model of FIG. 3.

The blood flow in this model was irradiated with a laser beam and the time-course variation of the scattered light received from the irradiated region was measured. The results obtained by measuring the flow velocity in accordance with Eq. 1 of the foregoing analysis procedure are shown in FIG. 4. As is clear from this figure, the results of the measurement lie on a straight line in substantial agreement with those obtained with the electromagnetic stromuhr. With prior calibration, therefore, it is possible to measure the absolute value of the blood flow velocity.

Figure 5:
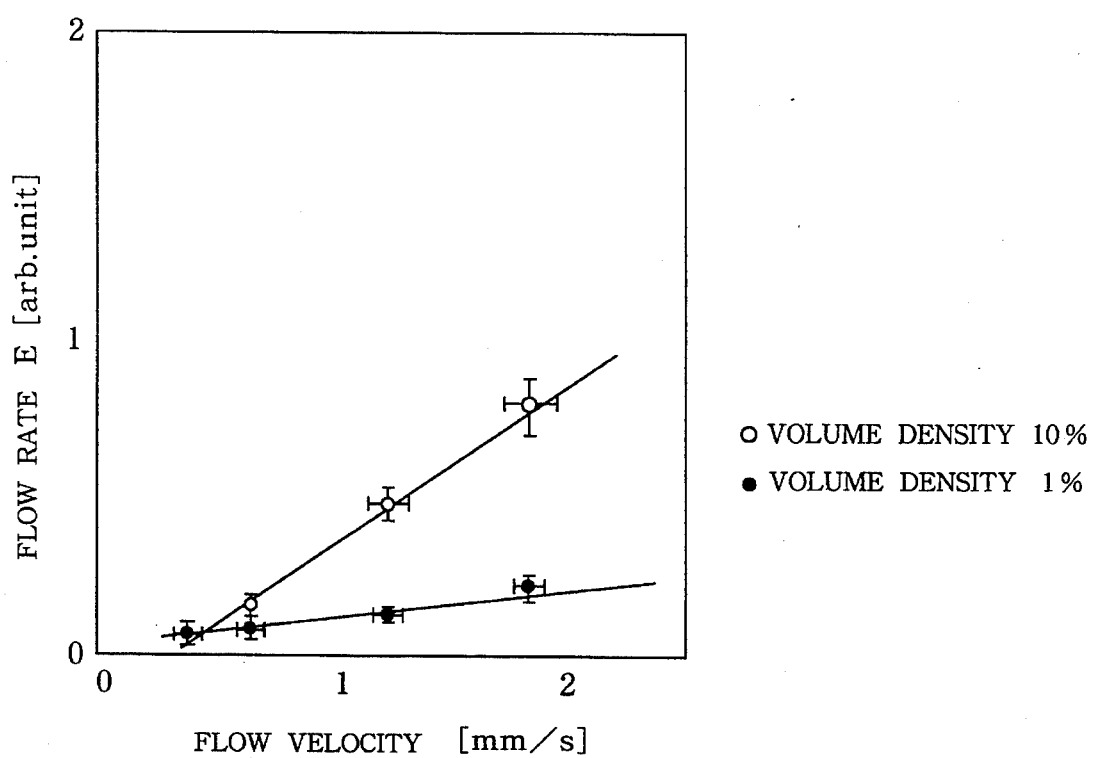
FIG. 5 is a graph showing the measurement results in the case where a suspension of polystyrene latex particles is passed through the model of FIG. 3 in place of blood.

FIG. 5 shows the results obtained when a suspension of polystyrene latex particles was passed through the silicon tube 1a of the model of FIG. 3 and the flow rate was measured based on Eq. 4 with the average flow velocity varied using the particle volume density as a parameter. As is clear from this Figure, the flow rate measured using this procedure varies depending upon the concentration and velocity of the suspended particles.

Thus, as explained in the foregoing, the power spectrum obtained from light-scattering particles flowing through a single tube can be accurately approximated as an exponential function. The analysis processing in which this function is fitted makes it possible to estimate the DC component of the power spectrum without using the power spectrum of the low-frequency region which is strongly affected by vibration and other types of noise. Since signal integration for noise component smoothing therefore becomes unnecessary, the analysis time is shortened.

When this method is applied to analysis of skin blood flow, therefore, it is possible to secure the same reduction in analysis time while also securing stability against vibration and other types of external disturbance.

By adopting the foregoing analysis method it is possible to measure skin blood flow as well as the blood flow rate in a single blood vessel. Differently from in the case of measuring blood flow rate in a single blood vessel, the absolute blood flow rate cannot be ascertained in skin blood flow measurement, however, because the crisscross pattern of the capillaries through which blood passes in the skin makes it impossible to obtain a complete exponential function for the power spectrum. Nevertheless, it is possible to achieve stable, rapid measurement of the blood flow rate in terms of the same measurement unit quantity as with a prior art laser stromuhr.

On the other hand, the absolute blood flow rate in an exposed blood vessel can be ascertained by defining the sectional area of the blood vessel in terms of the shape of the measurement probe, similarly to what is done in the case of the electromagnetic stromuhr.

In addition, when the blood vessel is irradiated with laser beams of different wavelengths, a quantity corresponding to the number of erythrocytes flowing through the blood vessel and their absorption property can be obtained from Eq. 3 for each wavelength. The value S corresponding to the number of erythrocytes is the power from the DC component of the scattered light intensity and, as such, is the effective value of the scattered light quantity. The ratio of the effective values of the scattered light quantities at two wavelengths is known to correspond to the ratio between the amounts of oxidized hemoglobin and reduced hemoglobin, i.e. to the degree of oxygen saturation. This means that it is possible also in the measurement of oxygen saturation degree to obtain stable measurement values free from the effect of vibration in the low-frequency region.

Figure 6A:
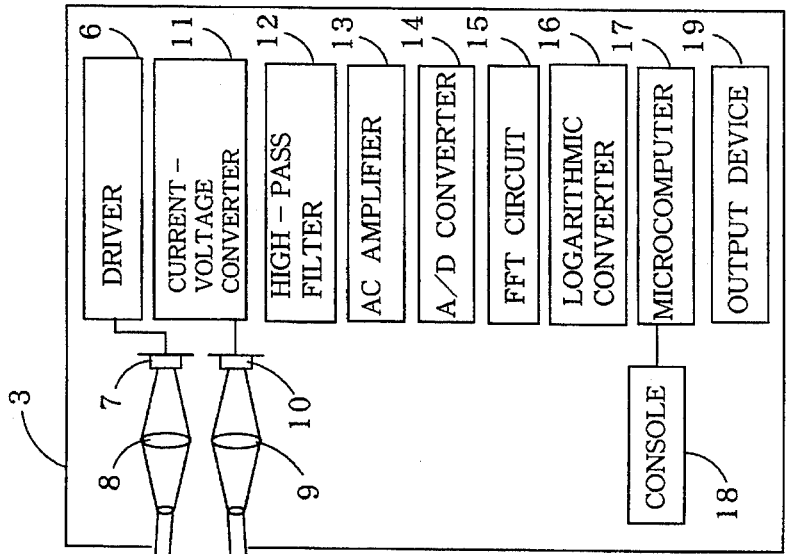
FIGS. 6a–b are schematic illustrative view, showing the overall arrangement of a blood flow measurement system according to the invention intended for measuring blood flow in a single blood vessel.
Figure 6B:
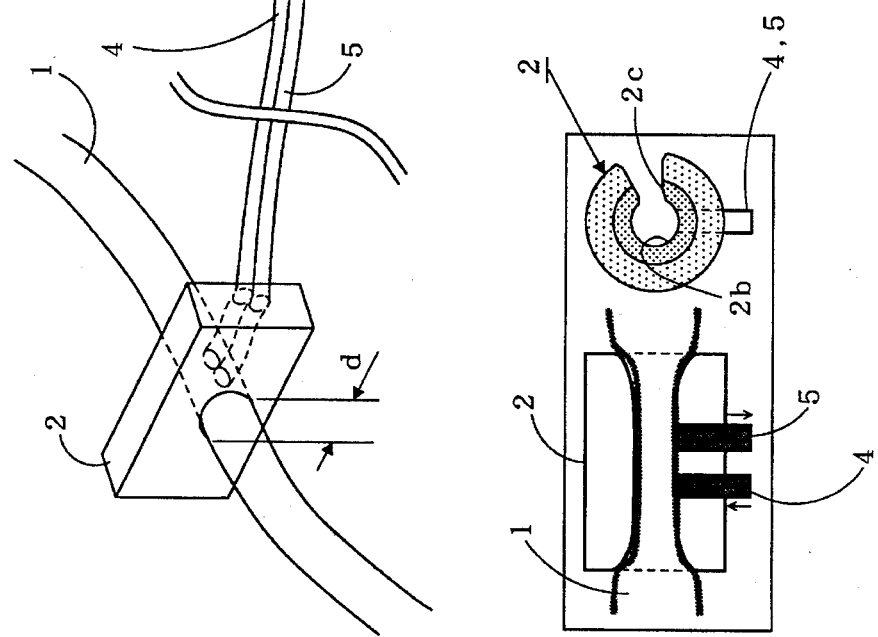

The specific arrangement of the system for working the invention will now be explained. FIG. 6 shows the general arrangement of an embodiment of the invention for use with a single blood vessel. The system of FIG. 6 comprises an analysis unit 3 and a measurement probe 2 for attachment to a blood vessel 1. The measurement probe 2 has a light-projecting optical fiber 4 and a light receiving optical fiber 5.

Although in FIG. 6 the light-projecting optical fiber 4 and the light-receiving optical fiber 5 enter the measurement probe in the same direction so that the light-receiving system receives light scattered to the rear, it is possible instead to use an arrangement in which the light-projecting system and the light-receiving system face each other so that light-receiving system receives light scattered forwardly or to use an arrangement for receiving light scattered to the side. A number of measurement probes 2 differing in internal diameter are prepared in advance and the one whose internal diameter best matches the outer diameter of the blood vessel concerned is selected for use in the measurement.

The measurement probe 2 has a cylindrical inner hole 2b with a slit 2c for permitting a blood vessel to be clamped in the inner hole 2b. To protect the blood vessel from damage, the opposite ends of the cylindrical inner hole 2b are curved outward. The middle portion of the inner hole 2b is formed straight for maintaining the diameter of the blood vessel constant. The light-projecting and light-receiving optical fibers 4, 5 open into the straight portion of the inner 2b hole. The fibers 4, 5 are disposed side by side in the longitudinal direction of the blood vessel.

The arrangement of the analysis unit 3 is shown at the right side of FIG. 6. A laser beam from a laser beam source 7 controlled by a drive circuit 6 is converged on one end of the light-projecting optical fiber 4 by a condenser lens 8, passes through the light-projecting optical fiber 4 and is projected onto the blood vessel 1 from the other end thereof. Light scattered by the erythrocytes (not shown) flowing through the blood vessel 1 passes through the light-receiving optical fiber 5 to be focused on a light-receiving element 10 by an image-forming lens 9. Although light is projected and received through optical fibers in the illustrated arrangement, it is alternatively possible to build the laser beam source 7 and the light-receiving element 10 into the measurement probe 2, in which case information is exchanged between the measurement probe 2 and the analysis unit 3 in the form of analog electric signals.

The photoelectric current from the light-receiving element 10 is converted to voltage by a current-voltage converter 11 and the resulting signal is passed through a high-pass filter 12 with a cutoff frequency of 100 Hz, passed through an AC amplifier 13 and converted to a digital signal by an A/D converter 14.

The converted digital signal is sent to an FFT (fast Fourier transform) circuit 15 for calculating the power spectrum. The power spectrum is subjected to logarithmic conversion in a logarithmic converter 16, whereafter its slope and height are calculated in a microcomputer 17 using the method of least squares.

At the same time, the blood flow rate is calculated based on the inside diameter (sectional area) of the measurement probe 2 input from a console 18 as $$F = \pi \left( \frac{d}{2} \right)^2 v \quad (5)$$

where:

F (mm³/s): Blood flow rate v (mm/s): Flow velocity determined by fitting d (mm): Sectional area of probe interior π: pi and the calculated value is output to an output device 19 such as a printer or a display.

While the blood flow rate is determined here from the product of the flow velocity and the sectional area of the measurement probe 2, it is also possible to determine the blood flow rate from Eq. 4, in which case prior calibration with an electromagnetic stromuhr or the like is required.

Figure 7:
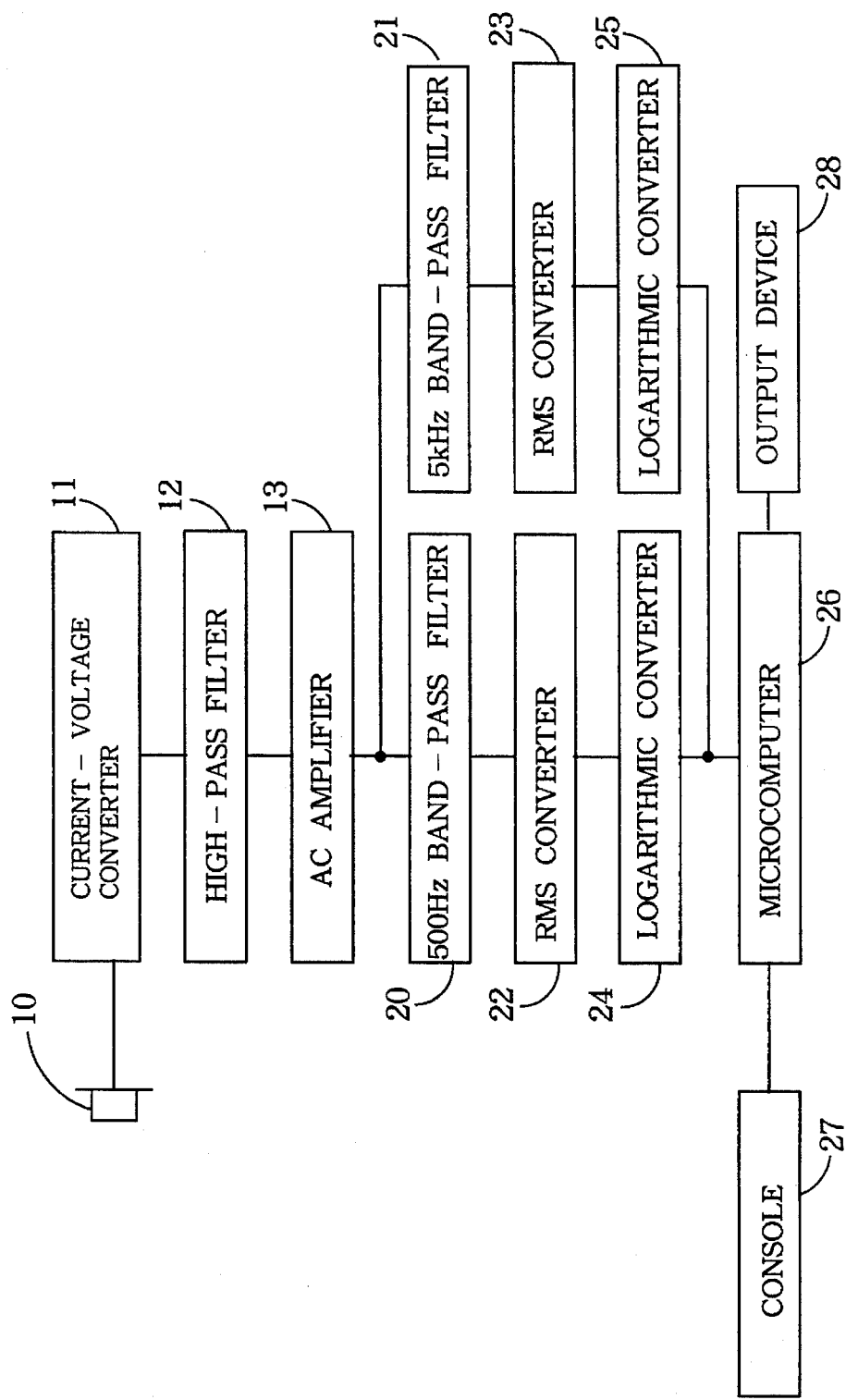
FIG. 7 is a block diagram showing the overall arrangement of a blood flow measurement system which conducts another kind of analysis processing.

FIG. 7 shows another arrangement of the circuit for analyzing the scattered light received. The arrangement according to FIG. 7 processes the signals for two nearby frequencies and is able to conduct blood flow measurement simply and quickly. Since this arrangement does not require an FFT circuit, moreover, it can be implemented at low cost.

In FIG. 7, the scattered light current signal from a light-receiving element 10 is converted to a voltage signal by a current-voltage converter 11. After the signal has been removed of its low-frequency component by a high-pass filter 12 with a cutoff frequency of 100 Hz, it is amplified by an AC amplifier 13 and sent through parallelly connected band-pass filters 20 and 21, which pass frequencies of 500 Hz and 5 kHz, respectively. The resulting AC signals are passed through an rms (root mean square) converter 22 and an rms converter 23 to obtain the effective values and the effective values are then converted to logarithmic values in logarithmic converters 24, 25.

Then, based on the logarithms of the effective values at the two frequency points, a microcomputer 26 calculates the blood flow rate from the slope of the semilogarithmic power spectrum and the y intercept, multiplies the so-obtained blood flow velocity by the sectional area of the blood vessel (which it ascertains from the inside diameter of the probe known from the probe type number input from a console 27), and outputs the product to an output device 28 as the blood flow rate at the position of the measurement probe 2.

In the aspects of the invention explained in the foregoing, the blood flow velocity or blood flow rate is determined by linear approximation with respect to the semilogarithmic power spectrum. Alternatively, however, it is possible to omit the logarithmic converter 16 from the arrangement of FIG. 6 or the logarithmic converters 24, 25 from the arrangement of FIG. 7 and determine the blood flow velocity or blood flow rate not by linear approximation but by exponential approximation based on Eq. 2, with the function fitting being conducted in the microcomputer 17 or the microcomputer 26.

Figure 8:
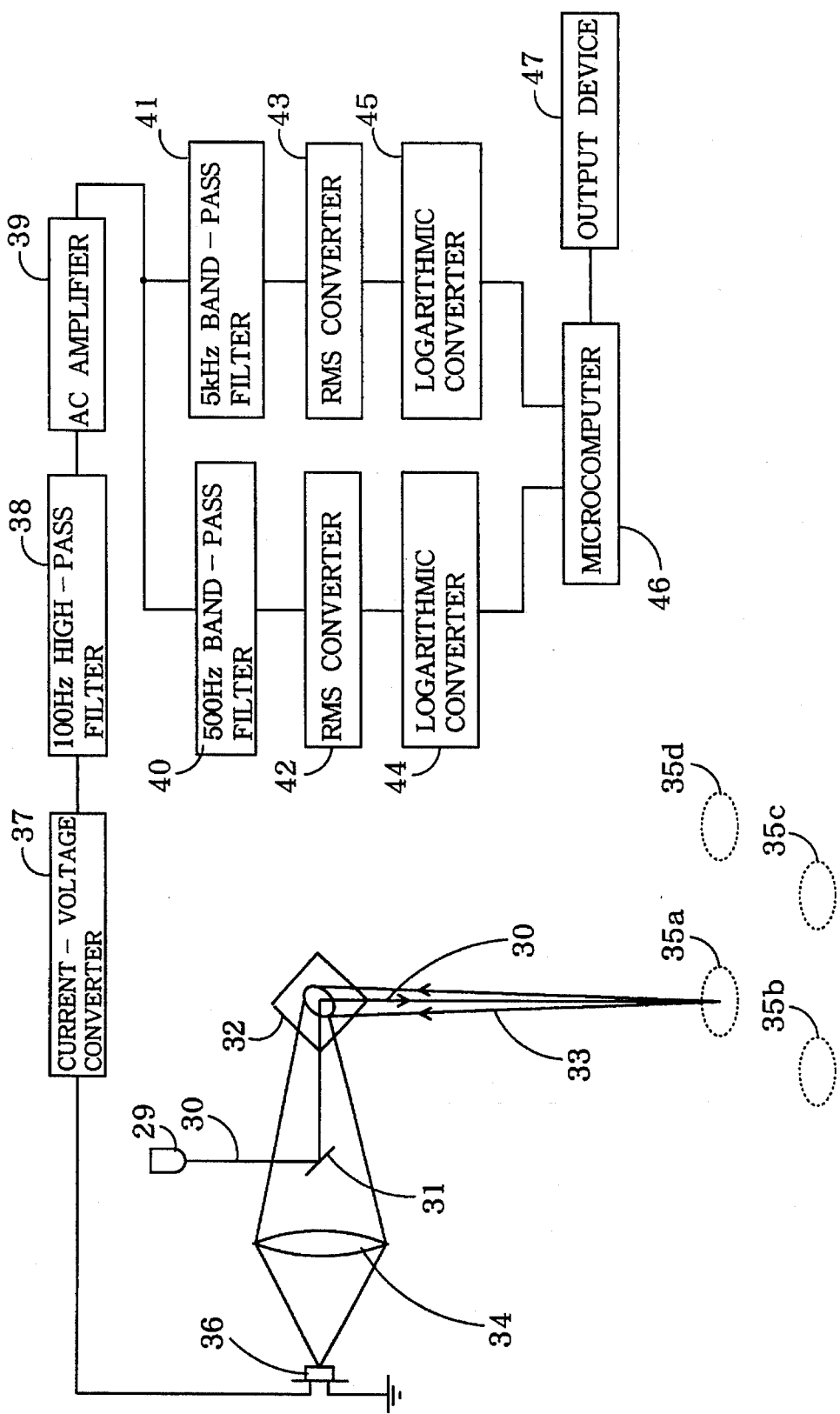
FIG. 8 is an illustrative diagram showing the overall arrangement of a blood flow measurement system for non-invasively measuring skin blood flow at multiple points.

FIG. 8 shows an arrangement for contactlessly measuring skin blood flow at multiple points (four points in the illustrated example). A laser beam 30 emitted from a laser beam source 29 and reflected by a mirror 31 is deflected by a scanner mirror 32 swung so as to successively position the laser beam 30 at different measurement points. The scanner mirror 32 is stopped at each of the measurement points and during each such rest period the scattered light 33 from the skin is reflected by the scanner mirror 32 through a light-receiving lens 34 to a light-receiving element 36 located at a position conjugate with four prescribed measurement points 35a to 35d. The light-receiving element 36 measures the time-course variation in the intensity of the scattered light. The scattered light from the skin consists of a scattered light component from stationary objects such as the skin tissue and a scattered light component from the erythrocytes flowing within the blood vessels.

While the intensities of the scattered light from the erythrocytes and the skin tissue both vary with time, the time-course variation in the intensity of the scattered light from the skin tissue, caused by respiration and the like, is slower than that in the intensity of the scattered light from the erythrocytes.

The photoelectric current from the light-receiving element 36 is converted to voltage in a current-voltage converter 37. After the signal has been removed of its low-frequency component by a high-pass filter 38 with a cutoff frequency of 100 Hz, it is amplified by an AC amplifier 39.

As in the arrangement of FIG. 7, the logarithms of the effective values at two frequencies, 500 Hz and 5 kHz, are determined. For this, the output of the AC amplifier 39 is passed through a 500 Hz band-pass filter 40 and a 5 kHz band-pass filter 41 to rms converters 42, 43, the outputs of which are the effective values.

The effective values are converted to logarithmic values in logarithmic converters 44, 45 and the blood flow velocity is determined by calculating the slope of the semilogarithmic power spectrum from the effective values at the two frequencies in a microcomputer 46.

Although, as can be seen from Eq. 4, the y intercept required for calculating the number of erythrocytes is necessary for further calculating the blood flow rate, this can be obtained from the slope of the power spectrum determined earlier.

While the y intercept is the logarithmic value of the DC light intensity, the DC light intensity does not have to be calculated directly from the measured value in the embodiment of FIG. 8 because the y intercept is calculated by linear approximation from the slope at a high frequency.

As was explained earlier, direct measurement of the DC light intensity in the low-frequency region gives scattered results owing to the effect of the vibration etc. of the subject caused by respiration and the like during the measurement. In the embodiment according to FIG. 8, however, the light intensity at low frequency is determined from that in the high-frequency region where stable measurement is possible, thereby enabling measurement unaffected by vibration. The values corresponding to the blood flows determined at the measurement points in the foregoing manner by use of only signals in the high-frequency region are output on a display, printer or other such output device 47.

Figure 9:
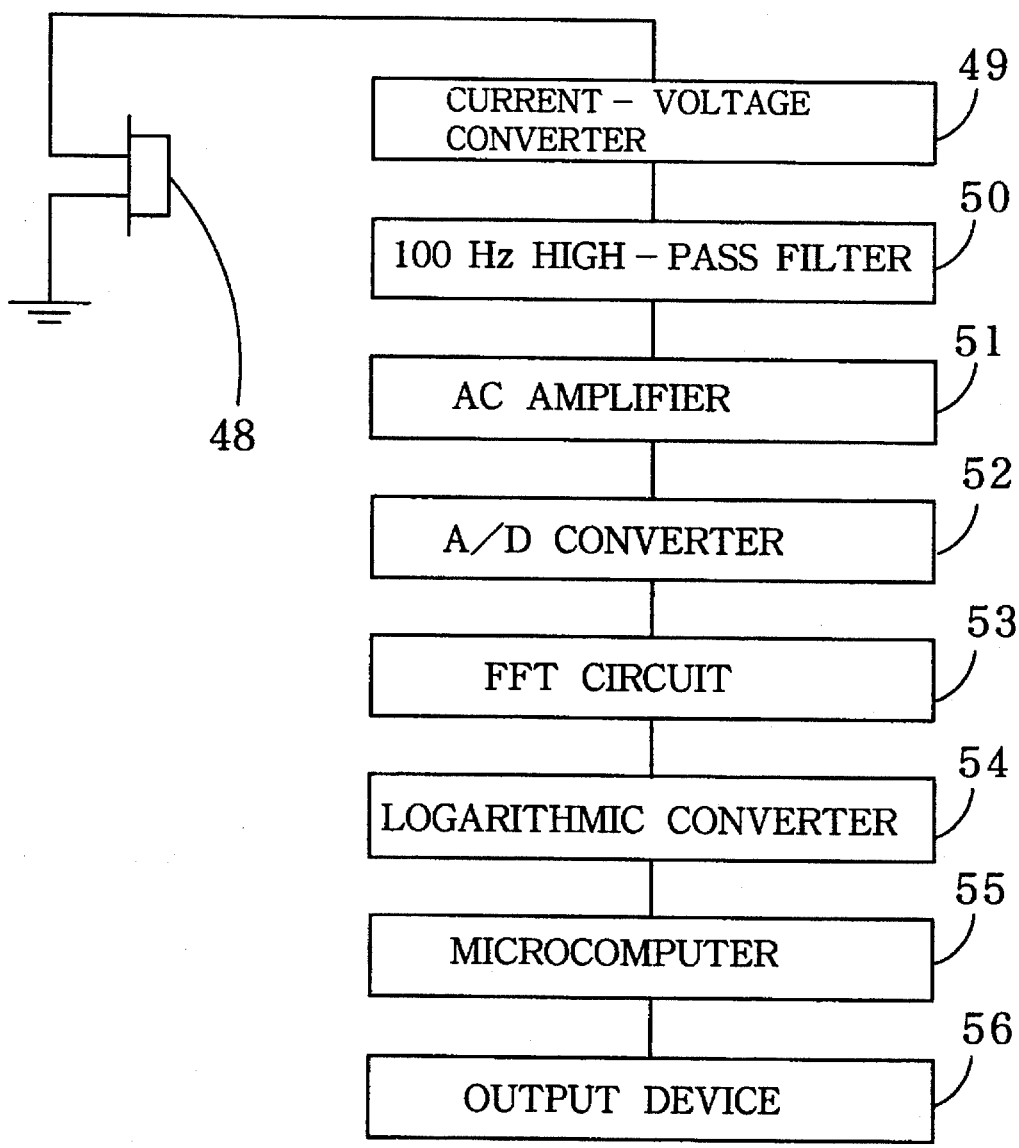
FIG. 9 is a diagram showing the overall arrangement of a blood flow measurement system which conducts another kind of analysis processing.

FIG. 9 shows another scattered light analysis system used for measuring blood flow at multiple points. The hardware arrangement of this system is nearly the same as that shown in FIG. 6. The photoelectric current from the light-receiving element 48 is converted to voltage by a current-voltage converter 49 and the resulting signal is passed through a high-pass filter 50 with a cutoff frequency of 100 Hz, passed through an AC amplifier 51 and converted to a digital signal by an A/D converter 52. The converted digital signal is sent to an FFT circuit 53 for calculating the power spectrum. The calculated power spectrum is subjected to logarithmic conversion in a logarithmic converter 54, whereafter the slope and y intercept of the power spectrum after linear approximation by the method of least squares are calculated in a microcomputer 55. The value corresponding to the blood flow is output to a display, printer or other such output device 56.

In the system of FIG. 9, the lower limit of the approximation region is set at several hundred Hz, preferably 500 Hz, so as to eliminate any effect from vibration and the like. The upper limit is set to be higher than a threshold whose value is determined by calculating an average value and a standard deviation of the noise voltage density in the high frequency region where the scattered light signal is obscured by noise and the power spectrum is flat and by adding twice the standard deviation to the average value. Further, the linear approximation is conducted after preprocessing for subtracting the average value of the noise from the power spectrum.

Since this analysis method enables the shape of the power spectrum to be obtained from that part of the time-course variation of the obtained scattered light intensity in the frequency region unaffected by vibration and the like, measurement can be conducted in a short period of time without prolonging the signal integration period. The method can therefore be applied with good effect in cases where, as described earlier with respect to FIG. 8, measurement is to be conducted at multiple points.

If the scanner mirror 32 used in the aforesaid multiple point measurement is replaced with a fixed mirror, measurement at a single point can be carried out in a contactless manner, i.e. without bringing a measurement probe into contact with the subject.

In the two embodiments just described, the blood flow velocity or blood flow rate is determined by linear approximation with respect to the semilogarithmic power spectrum. Similarly to the case of the earlier described embodiment for use with a single blood vessel, however, it is alternatively possible to omit the logarithmic converters 44, 45 from the arrangement of FIG. 8 or the logarithmic converter 54 from the arrangement of FIG. 9 and determine the blood flow velocity or blood flow rate not by linear approximation but by exponential approximation, with the approximation being conducted in the microcomputer 46 of FIG. 8 or the microcomputer 55 of FIG. 9.

A system arranged for outputting the oxygen saturation degree together with the blood flow rate will now be explained with reference to FIG. 10. Japanese Patent Laid-open Publication No. Hei 4(1982)-15046 discloses a method in which an in vivo tissue is irradiated with laser beams of different wavelengths and the oxygen saturation degree of the tissue is determined from the ratio of the effective values of the intensities of the scattered light from the erythrocytes. The present invention can also be effectively applied for calculating the effective values using the method of the foregoing Japanese Patent Laid-open Publication, namely, for calculating the area of the power spectrum.

Figure 10:
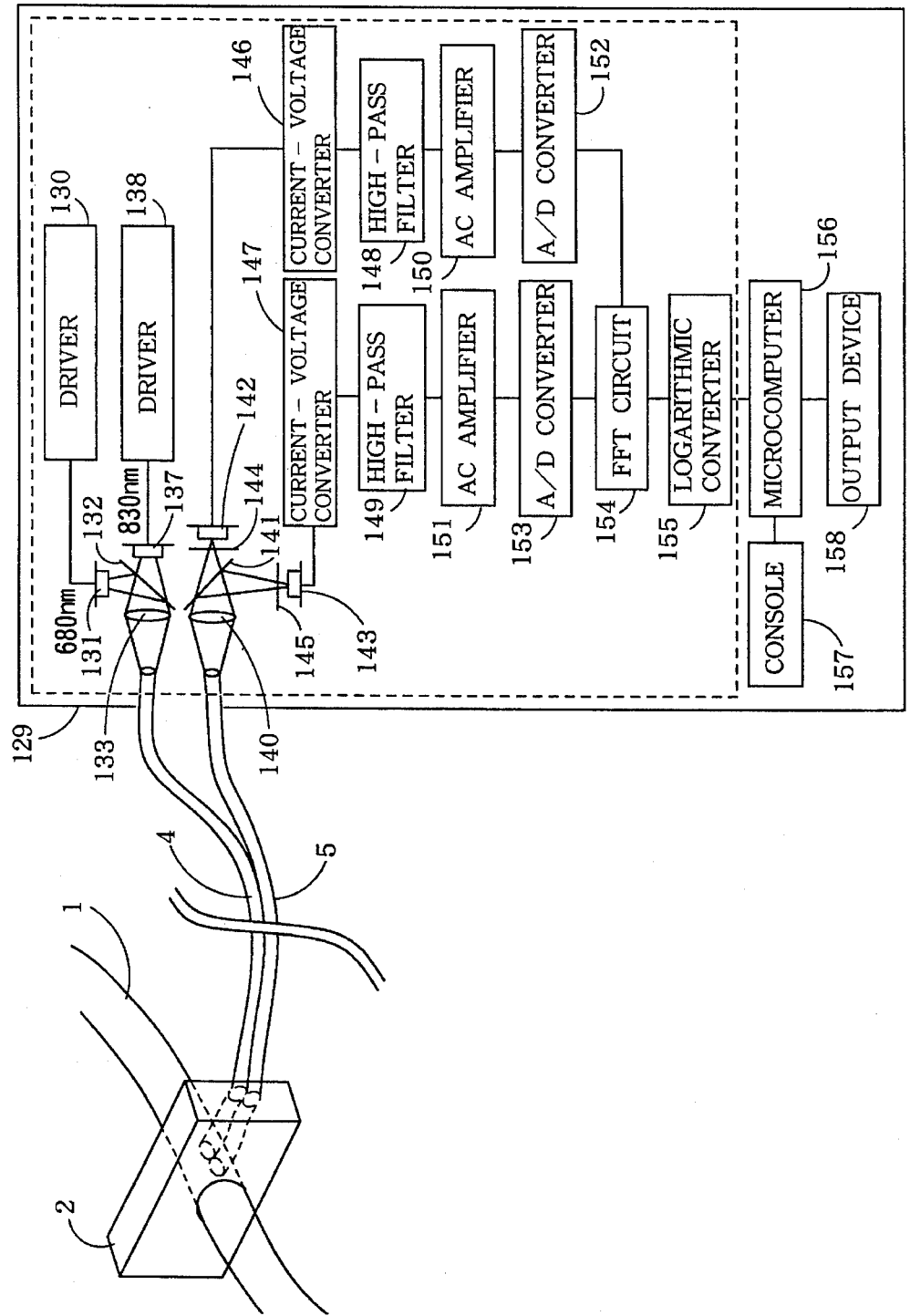
FIG. 10 is an illustrative diagram showing the overall arrangement of a blood flow measurement system that outputs the degree of oxygen saturation together with the blood flow rate.

The system shown in FIG. 10 is similar to that of FIG. 6 in that its measurement probe 2 is fitted on a blood vessel 1 but differs from it in the arrangement of an analysis unit 129.

A laser beam from a 680 nm semiconductor laser beam source 131 controlled by a drive circuit 130 is reflected by a half mirror 132 and converged by a condenser lens 133 onto one end of a light-projecting optical fiber 4 and, after passing through the light-projecting optical fiber 4, is projected from the other end thereof onto a blood vessel 1 fixed in position by a measurement probe 2.

Similarly, a laser beam source 137 emitting a laser beam of a different wavelength than the laser beam source 131, namely a laser beam with a wavelength of 830 nm, is power controlled by a drive circuit 138 to emit a laser beam through the half mirror 132. Like the 680 nm laser beam, this laser beam is also converged onto the light-projecting optical fiber 4 for irradiating the blood vessel 1.

A part of the scattered light from the erythrocytes (not shown) in the blood vessel 1 is absorbed by the erythrocytes. The amount of this absorption depends on whether the hemoglobin of the erythrocytes is in the oxidized or reduced state, while the characteristics of the absorption vary with the wavelength of the irradiating light.

The rays scattered by the erythrocytes and escaping absorption are picked up by a light-receiving optical fiber 5. The scattered light passing through and exiting from the other end of the light-receiving optical fiber 5 advances through an image-forming lens 140 to a half mirror 141 which splits it along two light paths.

The light along one of the paths advances through an interference filter 144 which passes only 680 nm light to a light-receiving element 142, while the light passing along the other path advances through an interference filter 145 to a light-receiving element 143 which passes only 830 nm light. Thus the 680 nm light is photoelectrically converted by the light-receiving element 142 and the 830 nm light is photoelectrically converted by the light-receiving element 143. The photoelectric current from the light-receiving element 142 is converted to voltage by a current-voltage converter 146 and the photoelectric current from the light-receiving element 143 is converted to voltage by a current-voltage converter 147. The resulting voltage signals are passed in parallel through high-pass filters 148, 149 and amplified by AC amplifiers 150, 151.

The amplified signals from the AC amplifiers 150, 151 are converted to digital values by A/D converters 152, 153. The converted digital signals are forwarded to an FFT circuit 154 for calculating the power spectra. The calculated power spectra are passed through a logarithmic converter 155 to a microcomputer 156 which calculates the slope and y intercept of the semilogarithmically expressed power spectrum at each wavelength and also calculates the effective value at each wavelength using Eq. 3.

The blood flow velocity is calculated from the slope at one of the wavelengths specified beforehand. The type number of the probe 2 is input to the microcomputer 156 from a console 157 as information indicating the inside diameter of the probe, and the microcomputer 156 calculates the blood flow rate from the inner diameter of the probe and the blood flow velocity in accordance with Eq. 5. The result is output to a display, printer or other such output device 158.

On the other hand, the numbers of erythrocytes calculated at the respective wavelengths using Eq. 3 are the effective values of the scattered light quantities at the respective wavelengths and the ratio between these numbers is a value corresponding to the oxygen saturation degree. This ratio is also output to the output device 158. The system arranged as shown in FIG. 10 can thus measure the oxygen saturation degree in addition to measuring the blood flow rate in the blood vessel.

The validity of the arrangement was checked with an in vivo model like that shown in FIG. 3, in which a Teflon block was used as an in vivo tissue model, a silicon tube was used as a blood vessel model, a peristaltic pump was used to produce a blood flow model, and preserved horse blood was used as a blood model.

In this model, the silicon tube was embedded in the Teflon block and the preserved horse blood was circulated through the tube by the peristaltic pump. As the oxygen saturation degree of the circulating blood was varied, the silicon tube was irradiated with 632.8 nm and 810 nm laser beams, the effective values of the scattered light intensities at the respective wavelengths were calculated using Eq. 3, and the scattered light intensity ratio was calculated and compared with the oxygen saturation degree.

Figure 11:
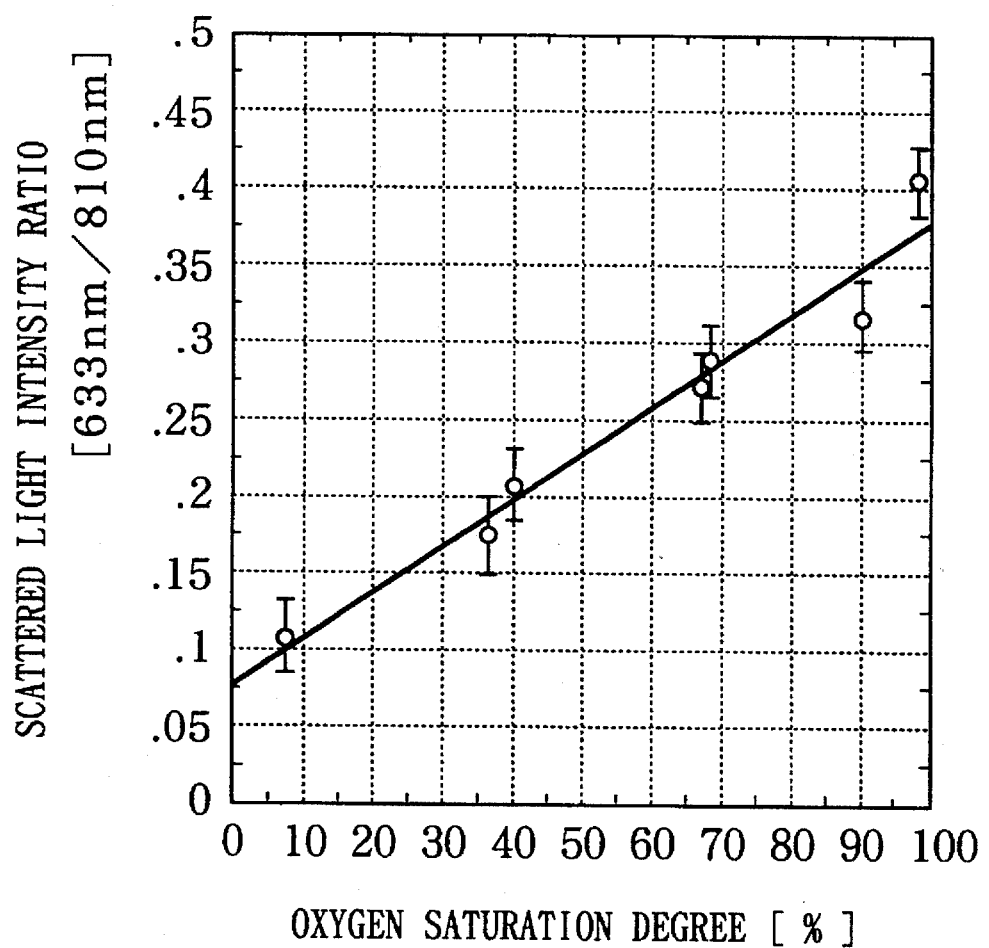
FIG. 11 is a graph showing an example of the degree of oxygen saturation measured with the system of FIG. 10.

The results are shown in FIG. 11, which shows the degrees of oxygen saturation obtained and the effective scattered light intensity ratios of the scattered light intensities at the respective wavelengths of the 632.8 nm and 810 nm laser beams used. As can be seen from FIG. 11, there is a good correlation between the ratio of the scattered light intensity of the dynamic speckle signal obtained from the power spectrum approximation equation and the oxygen saturation degree. By using this correspondence as the calibration curve it is possible to obtain the oxygen saturation degree.

Although the arrangement shown in FIG. 10 has only a single probe, the system can be adapted for multiple point measurement by equipping it with a plurality of measurement probes and analysis subunits.

In the case of measuring the oxygen saturation degree with two specified probes, for example, if one of them is attached to a typical nourishment-supplying artery of the tissue and the other is attached to a vein passing out of the tissue, the oxygen saturation degrees obtained from the probes can be compared to obtain an index for estimating the oxygen consumption state of the tissue.

The wavelengths of the irradiating beams used in the embodiment according to FIG. 10 do not necessarily have to be 680 nm and 830 nm as in the foregoing example. Other wavelengths can be used for specific purposes.

As will be understood from the foregoing description, the invention makes it possible to obtain information regarding blood flow rate, blood flow velocity and the like by determining the power spectrum of the time-course variation of the scattered light intensity and conducting specified function fitting with respect to prescribed frequency components of the power spectrum. In addition, by limiting the measurement to the specific frequency components of the power spectrums, vibration and other noise components can be prevented from affecting the measurement. The invention thus provides an excellent blood flow measurement system capable of conducting measurements accurately in a short period of time without being affected by vibration etc. of the in vivo tissue during the measurement and without the occurrence of induction between probes that arises in the electromagnetic stromuhr.

The present invention has thus been shown and described with reference to specific embodiments. However, it should be noted that the present invention is in no way limited to the details of the described arrangements but changes and modifications may be made without departing from the scope of the appended claims.

What is claimed is:

1. A blood flow measurement system for measuring blood flow rate and blood flow velocity comprising:

means for irradiating a in vivo tissue measurement subject with coherent light;

means for receiving scattered light from the in vivo tissue;

means for converting an intensity of the received scattered light into an electrical signal;

means for calculating a power spectrum of the time-course variation of the scattered light intensity based on the electrical signal;

means for plotting the power spectrum in a semilogarithmic coordinate system having a logarithmic vertical axis;

means for linearly approximating a prescribed frequency component of the semilogarithmic power spectrum and calculating a slope and a y intercept of the power spectrum curve; and means for calculating blood flow velocity from the slope of the curve approximating the power spectrum and calculating the blood flow rate from the slope and y intercept of the curve approximating the power spectrum.

2. A blood flow measurement system according to claim 1, wherein:

the irradiating means includes means for repeatedly spatially scanning a prescribed two-dimensional plane on the in vivo tissue measurement subject with the coherent light and momentarily stopping the coherent light to measure at a plurality of prescribed measurement points in the two-dimensional plane;

the means for receiving scattered light receives scattered light from the plurality of measurement points;

the means for converting the intensity of the received scattered light into an electrical signal measures the time-course variation of the scattered light intensity at each measurement point;

the means for calculating a power spectrum comprises a Fourier transform circuit for Fourier transforming the time-course variation;

the plotting means calculates a semilogarithmic power spectrum whose vertical axis is scaled logarithmically and whose frequency axis is scaled arithmetically;

the linear approximating means approximates a component of the power spectrum linearly above several hundred Hz and calculates the slope and y intercept of the approximated power spectrum; and the means for calculating the blood flow velocity and the blood flow rate calculates the blood flow velocity and the blood flow rate at the plurality of measurement points.

3. A blood flow measurement system according to claim 1, wherein:

the irradiating means includes means for irradiating a prescribed point on the in vivo tissue measurement subject with the coherent light;

the means for receiving scattered light receives scattered light from the prescribed point;

the means for converting the intensity of the received scattered light into an electrical signal measures the time-course variation of the scattered light intensity at the prescribed point;

the means for calculating a power spectrum comprises a Fourier transformation circuit for Fourier transforming the time-course variation;

the plotting means calculates a semilogarithmic power spectrum whose vertical axis is scaled logarithmically and whose frequency axis is scaled arithmetically;

the linear approximating means approximates a component of the power spectrum linearly above several hundred Hz and calculates the slope and y intercept of the approximated power spectrum curve; and the means for calculating the blood flow velocity and the blood flow rate calculates the blood flow velocity and the blood flow rate at the prescribed point from the calculated slope and y intercept.

4. A blood flow measurement system according to claim 1; further comprising a measurement probe having means for maintaining the diameter of a blood vessel of the in vivo tissue constant; and wherein:

the irradiating means irradiates the blood vessel with the coherent light;

the means for receiving scattered light receives scattered light from erythrocytes in the blood vessel;

the means for converting the intensity of the received scattered light into an electrical signal includes means for photoelectrically converting the scattered light received from the erythrocytes into a scattered light intensity variation electrical signal;

the means for calculating a power spectrum comprises a Fourier transform circuit for Fourier transforming the scattered light intensity variation electrical signal;

the plotting means calculates a semilogarithmic power spectrum whose vertical axis is scaled logarithmically and whose frequency axis is scaled arithmetically;

the linear approximating means approximates a component of the power spectrum above several hundred Hz and calculates the slope and y intercept of the approximated power spectrum curve; and the means for calculating the blood flow velocity and the blood flow rate calculates the blood flow velocity from the slope and calculates the blood flow rate from the blood flow velocity and a sectional area of the blood vessel determined from the constant blood vessel diameter maintained by the measurement probe.

5. A blood flow measurement system according to claim 1; wherein the linear approximating means comprises a fast Fourier transform circuit for calculating a scattered light intensity variation signal power spectrum and calculating the semilogarithmic power spectrum, the y intercept and slope of the semilogarithmic power spectrum curve being calculated by a method of least squares.

6. A blood flow measurement system according to claim 5; wherein the linear approximating means includes means for calculating an upper limit of the semilogarithmic power spectrum linear approximating region to a value higher than a signal intensity equal to the sum of a prescribed multiple of a standard deviation of the signal intensity in a prescribed high-frequency region where the signal density is flat and an average of the same signal intensity.

7. A blood flow measurement system according to claim 1; further comprising at least two sets each consisting of a band-pass filter, an effective value deriving circuit and a logarithmic converter, the band-pass filters of different sets having different band frequencies; and wherein the linear approximating means approximates a component of the semilogarithmic power spectrum curve above 500 Hz based on the outputs obtained by passing the scattered light intensity variation signal obtained through the at least two sets.

8. A blood flow measurement system for measuring blood flow rate and blood flow velocity comprising:

means for irradiating an in vivo tissue measurement subject with coherent light;

means for receiving scattered light from the in vivo tissue;

means for converting an intensity of the received scattered light into an electrical signal;

first calculating means for calculating a power spectrum of the time-course variation of the scattered light intensity based on the electrical signal;

means for exponentially approximating frequency components of the power spectrum above several hundred Hz and calculating a 1/e width and a DC intensity of the power spectrum; and second calculating means for calculating the blood flow velocity from the 1/e width of the power spectrum and calculating the blood flow rate from the 1/e width and the DC intensity obtained by exponential approximation of the power spectrum.

9. A blood flow measurement system according to claim 8, wherein:

the irradiating means includes means for repeatedly spatially scanning a prescribed two-dimensional plane on the in vivo tissue measurement subject with the coherent light and momentarily stopping the coherent light to measure at a plurality of prescribed measurement points in the two-dimensional plane;

the means for receiving scattered light receives scattered light from the plurality of measurement points;

the means for converting the intensity of the received scattered light into an electrical signal measures the time-course variation of the scattered light intensity at each measurement point;

the means for calculating a power spectrum comprises a Fourier transform circuit for Fourier transforming the time-course variation; and the means for calculating the blood flow velocity and the blood flow rate calculates the blood flow velocity and the blood flow rate at the plurality of measurement points.

10. A blood flow measurement system according to claim 8, wherein:

the irradiating means includes means for irradiating a prescribed point on the in vivo tissue measurement subject with the coherent light;

the means for receiving scattered light receives scattered light from the prescribed point;

the means for converting the intensity of the received scattered light into an electrical signal measures the time-course variation of the scattered light intensity at the prescribed point;

the means for calculating a power spectrum comprises a Fourier transform circuit for Fourier transforming the time-course variation; and the means for calculating the blood flow velocity and the blood flow rate calculates the blood flow velocity and blood flow rate at the prescribed point from the slope and y intercept of the power spectrum curve.

11. A blood flow measurement system according to claim 8; further comprising a measurement probe having means for maintaining the diameter of a blood vessel of the in vivo tissue constant; and wherein:

the irradiating means irradiates the blood vessel with the coherent light;

the means for converting the intensity of the received scattered light into an electrical signal includes means for photoelectrically converting the scattered light received from the erythrocytes into a scattered light intensity variation electrical signal;

the means for calculating a power spectrum comprises a Fourier transform circuit for Fourier transforming the scattered light intensity variation electrical signal; and the means for calculating the blood flow velocity and the blood flow rate calculates the blood flow velocity from the 1/e width and calculates the blood flow rate from the blood flow velocity and a sectional area of the blood vessel determined from the constant blood vessel diameter maintained by the measurement probe.

12. A blood flow measurement system according to claim 8; wherein the exponential approximating means comprises a Fourier transform circuit for calculating a power spectrum, the DC intensity and 1/e width of the exponential function being calculated by a method of least squares.

13. A blood flow measurement system according to claim 8; further comprising at least two sets each consisting of a band-pass filter, an effective value deriving circuit and a logarithmic converter, the band-pass filters of different sets having different band frequencies; and wherein the exponential approximating means approximates the power spectrum based on the outputs obtained by passing the scattered light intensity variation signal obtained through the at least two sets.

14. A blood flow measurement system according to claim 8; wherein the exponential approximating means includes means for approximating a logarithm of the calculated power spectrum by a method of least squares to a straight line whose slope and y intercept are respectively used to determine the 1/e width and DC intensity of the power spectrum.

15. A blood flow measurement system according to claim 14; wherein the linear approximating means includes means for calculating an upper limit of the approximation region to a value higher than a signal intensity equal to the sum of a predetermined multiple of a standard deviation of the signal intensity in a predetermined high-frequency region where the signal density is flat and an average of the same signal intensity.

16. A blood flow measurement system according to claim 8; wherein the exponential approximating means includes means for extracting first and second frequency components of the power spectrum and converting the first and second frequency components to logarithmic values to determine a straight line whose slope and y intercept are respectively used to determine the 1/e width and DC intensity of the power spectrum.

17. A blood flow measurement system according to claim 8; wherein the irradiating means includes means for repeatedly spatially scanning the coherent light in a two-dimensional plane on the in vivo tissue measurement subject and momentarily stopping the coherent light at a plurality of predetermined measurement points to measure the time-course variation of the scattered light intensity.

18. A blood flow measurement system according to claim 8; wherein the irradiating means includes means for irradiating the coherent light on a predetermined point on the in vivo tissue measurement subject, and the receiving means receives the scattered light from the predetermined point to measure the time-course variation of its intensity.

19. A blood flow measurement system according to claim 8; wherein the irradiating means includes means for irradiating the coherent light on a predetermined point on a blood vessel of the in vivo tissue measurement subject, and the receiving means receives the scattered light from the predetermined point to measure the time-course variation of its intensity.

20. A blood flow measurement system according to claim 8; wherein the irradiating means includes means for irradiating a single blood vessel of the in vivo tissue measurement region with coherent light of two or more wavelengths, the first calculating means calculates the power spectrum for each wavelength, and the exponential approximating means approximates the power spectrum to the exponential function, the approximated power spectrum of one wavelength being used to determine the blood flow velocity and blood flow rate and combined with the approximated power spectrum of another wavelength to determine the degree of oxygen saturation of the single blood vessel.

21. A blood flow measurement system comprising:

means for irradiating a single blood vessel with coherent light of at least two wavelengths;

means for receiving scattered light of each wavelength from erythrocytes in the blood vessel;

at least one measurement probe having means for maintaining the diameter of the blood vessel constant;

means for photoelectrically converting the scattered light of each wavelength from the erythrocytes into a scattered light intensity variation electrical signal;

means for calculating a power spectrum of the scattered light intensity variation electrical signal by Fourier transform;

means for plotting a semilogarithmic power spectrum whose vertical axis is scaled logarithmically and whose frequency axis is scaled arithmetically;

means for linearly approximating a component of the power spectrum above several hundred Hz and calculating the slope and y intercept of the approximated power spectrum curve; and means for calculating blood flow velocity from the slope of the curve approximating the power spectrum, calculating blood flow rate from the blood flow velocity and a sectional area of the blood vessel determined from the constant blood vessel diameter maintained by the measurement probe, and calculating the degree of oxygen saturation by calculating an absorption degree for each wavelength by comparing integrated intensities calculated from the product of the slopes and the y intercepts of the power spectrums at the two wavelengths.

* * * * *